United States Patent
Rahman

(10) Patent No.: US 6,193,515 B1
(45) Date of Patent: Feb. 27, 2001

(54) CODED DENTAL HANDLE

(75) Inventor: Anis Rahman, Gurnee, IL (US)

(73) Assignee: Hu-Friendly Mfg. Co., Inc., Chicago, IL (US)

( * ) Notice: Subject to any disclaimer, the term of this patent is extended or adjusted under 35 U.S.C. 154(b) by 0 days.

(21) Appl. No.: 09/451,522

(22) Filed: Nov. 30, 1999

(51) Int. Cl.[7] .................................................. A61C 3/00
(52) U.S. Cl. ............................................ 433/141; 433/72
(58) Field of Search ................................... 433/141, 146, 433/72, 75, 102

(56) References Cited

U.S. PATENT DOCUMENTS

| | | | |
|---|---|---|---|
| 4,882,867 | 11/1989 | Linden . | |
| 4,988,295 | * 1/1991 | Kline | 433/141 |
| 5,090,907 | * 2/1992 | Hewitt et al. | 433/141 X |
| 5,498,158 | * 3/1996 | Wong | 433/102 |
| 5,501,597 | * 3/1996 | Wilson | 433/141 |
| 5,816,806 | * 10/1998 | Herbst et al. | 433/141 |
| 5,842,861 | * 12/1998 | Buchanan | 433/102 |

* cited by examiner

*Primary Examiner*—Nicholas D. Lucchesi
(74) *Attorney, Agent, or Firm*—Rockey, Milnamow & Katz, Ltd.

(57) ABSTRACT

A color coded elastomeric ring is fit onto a dental instrument. The elastomeric ring includes axial and circumferential formations for increased traction of a dental practitioner's finger to manipulate the instrument. Advantageously, two elastomeric rings are provided, one at each end of the instrument. Each elastomeric ring preferably has an outside profile with a decreasing diameter toward the adjacent end of the instrument. The ring is located adjacent to a receiving port for a tool insert or point.

23 Claims, 1 Drawing Sheet

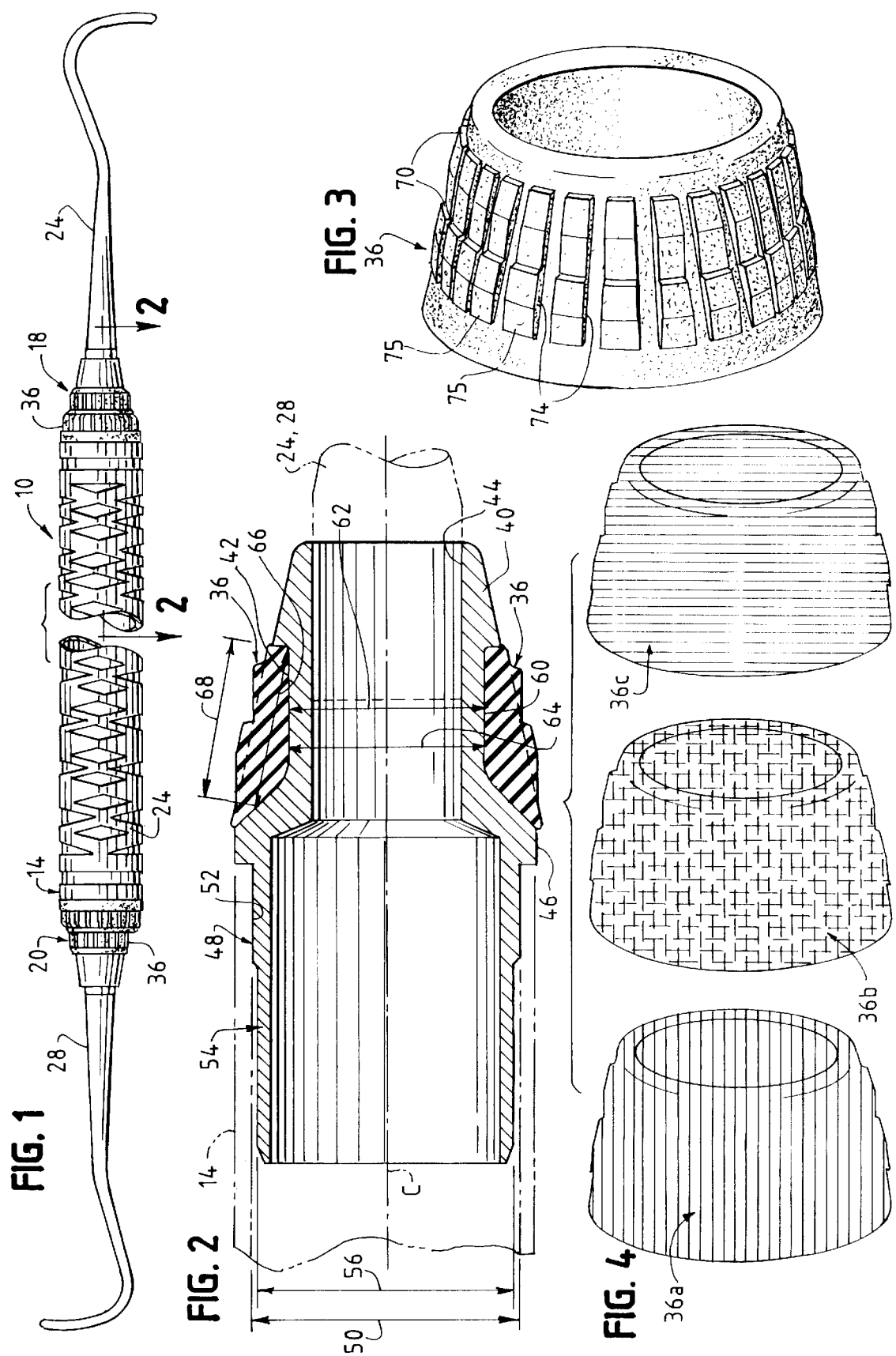

CODED DENTAL HANDLE

TECHNICAL FIELD OF THE INVENTION

The invention is directed to hand held dental instruments. Particularly, the invention is directed to a color coded handle feature for dental instruments.

BACKGROUND OF THE INVENTION

Dental practitioners often organize instruments for various reasons. The instruments are sometimes organized or sorted according to steps in the procedure to be performed by the practitioner. The instruments could alternatively be sorted by ownership in a situation where dental practitioners share equipment. Color coding is one method of organizing or sorting such instruments.

Known dental instruments are composed of metal and can be difficult to color code. Coloring metal instruments can be done by black oxidation or by plating. However, these methods are costly, inefficient, and offer limited color choices depending on the base metal alloy. Such coloring techniques can have a short effective life due to repeated sterilization of the dental instrument. The coating or plating may crack from repeated thermal cycles during sterilization and may eventually peel from the base metal.

The present inventor recognized the need for providing a cost effective color coding system for sorting and organizing dental instruments. Additionally, the present inventor recognized the need for increasing the practitioner's finger dexterity and control of the dental instrument and the need for decreasing finger fatigue due to prolonged gripping of the instrument.

SUMMARY OF THE INVENTION

According to the present invention, a color coded elastomeric ring is fit over a portion of a dental instrument. The ring is advantageously composed of a material which is repeatably sterilizable. The ring can be color coded according to a wide array of colors.

The ring, being composed of a soft, stretchable material, can be stretched over the instrument ends and consequently can be installed or replaced quickly and easily. The ring can be replaced in a dental practitioner's office, if necessary. The elastomeric ring fits onto a tool-receiving end portion of the instrument handle. The end portion has a port that receives a tool insert. The ring is preferably composed of silicone.

The elastomeric ring has surface formations which promote gripping and manipulation of the instrument. Circumferential ridges provide for positive traction of fingers for rotational movement and control of the instrument. This traction is particularly significant since a dental practitioner can be holding the instrument through slippery, saliva-coated gloves.

Steps along an axial direction on the elastomeric ring provide for precise axial location of the practitioner's fingers with respect to the instrument. Axial location is important to the practitioner to receive a positive feedback of the location of the instrument inside a patient's mouth.

The soft elastomeric ring reduces finger stress from prolonged gripping by the practitioner.

According to one embodiment, a dental instrument includes a handle shaft and two opposite end portions with a tool insert, such as a "point", carried by each of the opposite end portions. Each end portion forms the interface between the tool insert and the handle shaft. One elastomeric ring is mounted around each of the two end portions of the instrument.

Each end portion includes a "cone", or socket portion, for receiving the tool insert, a neck portion extending from the cone, a base portion connected to the neck portion, and a plug portion connected to the base portion, all as a unitary piece that is symmetrical about its central axis. The plug portion connects to an end of a handle shaft. The cone, the neck portion and the base portion define a groove that is complimentary to the shape of the elastomeric ring and sized such that it provides for a secure fit therebetween. The inner diameter of the elastomeric ring is somewhat smaller than the outer diameter of a floor of the groove, thereby providing a stretched radial fit. The elastomeric ring is also somewhat wider than the groove in an axial direction to allow an interference fit in the axial direction. The relative size of the ring and groove insures minimal debris entrapment between the ring and the groove.

Other features and advantages of the present invention will become readily apparent from the following detail description, the accompanying drawings, and the appended claims.

BRIEF DESCRIPTION OF THE DRAWINGS

FIG. 1 is an elevational view of a dental instrument incorporating the present invention;

FIG. 2 is an enlarged sectional view taken from FIG. 1;

FIG. 3 is an enlarged perspective view of an elastomeric ring taken from FIG. 1; and FIG. 4 is a perspective view of a plurality of color coded rings.

DETAILED DESCRIPTION OF THE PREFERRED EMBODIMENTS

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

FIG. 1 illustrates a dental instrument 10 having a handle shaft 14, substantially identical end portions 18, 20 connected to opposite ends of the handle shaft 14, and corresponding tool inserts or "points" 24, 28 connected to the end portions 18, 20, respectively. The tool inserts 24, 28 can be selected from a variety of dental tools depending on the procedure to be performed. The handle shaft 14 can include grooves 32 of varying widths arranged in a pattern on an outside surface of the handle, or other surface treatment, to promote gripping "traction" of the dental practitioner's fingers. The handle shaft 14, as a component of the instrument 10, is a hollow tubular member having open ends.

As illustrated in FIGS. 1 and 2, each end portion 18, 20 is surrounded by an elastomeric ring 36.

The elastomeric rings are preferably composed of silicone that can be color coded easily for the desired procedure or for other reasons. The elastomeric material is also advantageously composed of a material that is repeatably sterilizable, such as silicone.

Referring to FIG. 2, the end portions 18, 20 are rotationally symmetrical about a centerline C. Each end portion 18, 20 includes a cone 40 transitioning to a neck 42. The cone 40 includes a port 44 for receiving one of the respective tool inserts or points 24, 28. The tool insert is fit into the port and fixed therein by press fitting, braising, welding, adhesive or other technique. The neck 42 is transitions to a tapered base portion 46 which is connected to a plug portion 48.

The plug portion 48 is substantially cylindrical and has a maximum outside diameter 50 sized to fit within an open end 52 of the handle 14. The plug portion has a brazing end portion 54 with a reduced diameter 56 which allows for a gap 57 between an outside of the plug portion and an inside of the handle 14 to receive brazing compound to braze the end portion 18, 20 and the handle 14 together. The cone 40, the neck 42 and the base portion 46 define an annular groove 60 which is shaped to receive one of the elastomeric rings 36. The groove has a base diameter 62 which is greater than a relaxed inside diameter 64 of the elastomeric ring. A width 66 of the elastomeric ring is slightly greater than a width 68 of the groove 60. Thus, when the ring is fit into the groove, the ring is gripped tightly by the groove in both a radial and an axial direction by the groove. Also, the tight fit between the ring 36 and the groove 60 prevents entrapment of particles or debris between the ring and the end portion, advantageous for sanitary reasons.

The depth dimension of the groove is sized such that the thinnest wall thickness in the end portion is no thinner than the wall thickness of the handle, insuring no weak spot on the end portion.

Each ring 36 is advantageously composed of silicone to be stretchable to be fit tightly into the groove. Because the ring is stretchable, it can be replaced by forcibly removing the old ring from the groove and axially over the cone and the point (or the point can be removed before removing or installing a ring). A new ring can then be forced over the point and the cone and into the groove.

As illustrated in FIG. 3, the rings include a plurality of axial steps 70, and a plurality of circumferential ridges 74 formed by axially extending, circumferentially spaced apart platforms 75. The axial steps 70 allow for precise axial control and positions of the instrument within a patient's mouth. The circumferential ridges 74 allow for precise rotary positioning and control within a patient's mouth.

FIG. 4 illustrates a plurality of elastomeric rings 36a, 36b, 36c composed of three different colors. These colors can be selected according to the desired service, procedural step or to indicate practitioner ownership, or for any other purpose.

From the foregoing, it will be observed that numerous modifications and variations can be effected without departing from the true spirit and scope of the novel concept of the present invention. It is to be understood that no limitation with respect to the specific embodiment illustrated herein is intended or should be inferred. The disclosure is intended to cover, by the appended claims, all such modifications as fall within the scope of the claims.

The invention claimed is:

1. A dental instrument, comprising:

a handle;

an asymmetrical tool connected to said handle; and a plurality of color coded rings, a selected one of which is fit onto said handle, wherein said one ring includes circumferentially arranged ridges for finger traction, said circumferentially arranged ridges providing precise rotational positioning of said asymmetrical tool within a patient's mouth.

2. The dental instrument according to claim 1, wherein said one ring includes axial steps for finger traction.

3. The dental instrument according to claim 1, comprising at least one end portion connected to said handle, said tool connected to said end portion, and said one ring is fit onto said end portion.

4. A dental instrument, comprising:

a handle;

at least one end portion connected to said handle;

a tool connected to said end portion; and a plurality of color coded rings, a selected one of which is fit onto said handle, said one ring is fit onto said end portion; and wherein said end portion includes a circumferential groove, and said one ring fits at least partially into said groove.

5. The dental instrument according to claim 4, wherein said groove has a cylindrical outer surface, and said one ring has a cylindrical inner surface that is sized to be stretched to fit onto said cylindrical outer surface.

6. The dental instrument according to claim 4, wherein said one ring is located adjacent to said tool and is provided with gripping surface formations.

7. A dental instrument, comprising:

a handle;

a tool connected to said handle; and a plurality of color coded rings, a selected one of which is fit onto said handle, wherein said one ring has a decreasing diameter profile along its axis toward said tool.

8. The dental instrument according to claim 7, wherein said one ring includes axial steps for finger traction.

9. The dental instrument according to claim 7, wherein said one ring includes circumferentially arranged ridges for finger traction.

10. The dental instrument according to claim 9, wherein said one ring includes axial steps for finger traction.

11. A dental instrument, comprising:

a handle;

a tool connected to said handle; and an elastomeric ring fit onto said handle, said ring being rotationally symmetrical about a longitudinal centerline of said handle and having raised surface formations thereon forming circumferentially spaced gripping surfaces for precisely positioning said tool within a patient's mouth.

12. The dental instrument according to claim 11, wherein said surface formations include axial steps for finger traction.

13. The dental instrument according to claim 11, wherein said surface formations include circumferentially aligned ridges.

14. The dental instrument according to claim 11, comprising at least one end portion connected to said handle, said tool connected to said end portion, and said ring is fit onto said end portion.

15. The dental instrument according to claim 14, wherein said end portion includes a circumferential groove, and said elastomeric ring fits at least partially into said groove.

16. The dental instrument according to claim 15, wherein said groove has a cylindrical outer surface, and said ring has a cylindrical inner surface that is sized to be stretched to fit onto said cylindrical outer surface.

17. The dental instrument according to claim 11, wherein said ring is located adjacent to said tool.

18. The dental instrument according to claim 11, wherein said elastomeric ring is a selected one of a plurality of elastomeric rings each having a different color.

19. The dental instrument according to claim 11, wherein said elastomeric ring is composed of silicone.

20. A dental instrument, comprising:
a handle;
a tool connected to said handle; and
an elastomeric ring fit onto said handle,
wherein said ring has a tapered profile along its axis.

21. The dental instrument according to claim 20, wherein said ring includes axial steps for finger traction.

22. The dental instrument according to claim 20, wherein said ring includes circumferentially arranged ridges for finger traction.

23. The dental instrument according to claim 22, wherein said ring includes axial steps for finger traction.

* * * * *